United States Patent [19]

Duggan

[11] Patent Number: 4,921,974
[45] Date of Patent: May 1, 1990

[54] INTERMEDIATES AND PROCESSES IN THE PREPARATION OF 5-OXYGENATED HMG-COA REDUCTASE INHIBITORS

[75] Inventor: Mark E. Duggan, Wynnewood, Pa.

[73] Assignee: Merck & Co., Inc., Rahway, N.J.

[21] Appl. No.: 250,646

[22] Filed: Sep. 29, 1988

[51] Int. Cl.$^5$ .............................................. C07F 7/18
[52] U.S. Cl. .................... 549/214; 549/292; 544/58.4; 544/69; 544/149; 544/229; 544/374; 546/14; 546/206; 548/406; 548/517
[58] Field of Search ............... 549/214, 292; 514/460, 514/63; 546/206, 14; 544/374, 229, 69, 149, 58.4; 548/406, 517

[56] References Cited

U.S. PATENT DOCUMENTS

| | | | |
|---|---|---|---|
| 4,588,715 | 5/1986 | Damon, II | 549/292 |
| 4,604,472 | 8/1986 | Ide et al. | 549/292 |
| 4,710,513 | 12/1987 | Willard et al. | 549/292 |
| 4,733,003 | 3/1988 | Ide et al. | 568/119 |

FOREIGN PATENT DOCUMENTS

| | | | |
|---|---|---|---|
| 188872 | 11/1983 | Japan | 549/214 |
| 2075013 | 11/1981 | United Kingdom . | |

Primary Examiner—Richard L. Raymond
Assistant Examiner—Mark W. Russell
Attorney, Agent, or Firm—Melvin Winokur; Joseph F. DiPrima

[57] ABSTRACT

This invention relates to novel intermediates and novel processes for their preparation where said intermediates are useful in the preparation of 5'-oxygenated derivatives (I) of lovastation and analogs thereof at the 8'-acyl side chain and 6'-position of the polyhydronaphthyl ring. Derivatives (I) and analogs thereof are useful in treating hypercholesterolemia.

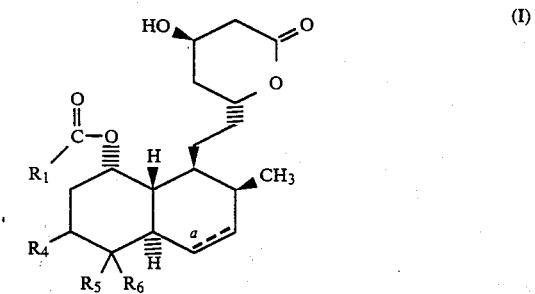

8 Claims, No Drawings

INTERMEDIATES AND PROCESSES IN THE PREPARATION OF 5-OXYGENATED HMG-COA REDUCTASE INHIBITORS

BACKGROUND OF THE INVENTION

Hypercholesterolemia is known to be one of the prime risk factors for ischemic cardiovascular disease, such as arteriosclerosis. Bile acid sequestrants have been used to treat this condition; they seem to be moderately effective but they must be consumed in large quantities, i.e. several grams at a time, and they are not very palatable.

MEVACOR® (lovastatin), now commercially available, in one of a group of very active antihypercholesterolemic agents that function by limiting colesterol biosynthesis by inhibiting the enzyme, HMG-CoA reductase. In addition to the natural fermentation products, mevastatin and lovastatin, there are a variety of semi-synthetic and totally synthetic analogs thereof.

The naturally occurring compounds and their semi-synthetic analogs have the following general structural formulae:

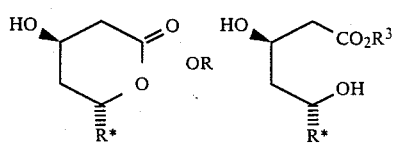

wherein:

$R_3$ $l$ is hydrogen, $C_{1-5}$ alkyl or $C_{1-5}$ alkyl substituted with a member of the group consisting of phenyl, dimethylamino, or acetylamino; and

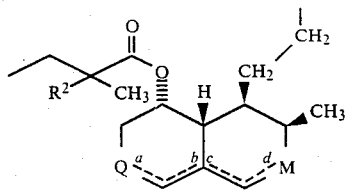

wherein Q is

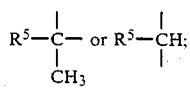

$R^5$ is H or OH; M is

$R^6$ is hydrogen or hydroxy;
$R^2$ is hydrogen or methyl; and a, b, c, and d represent single bonds, one of a, b, c or d represents a double bond, or both a and c or both b and d represent double bonds provided that when a is a double bond, Q is

or

and when d is a double bond, M is

U.K. Pat. No. 2,075,013 discloses semi-synthetic hydroxy containing compounds represented by the above general formula wherein R* is:

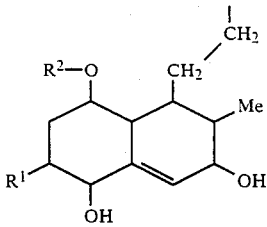

wherein $R^1$ is H or Me, and $R^2$ is H or acyl.

U.S. patent application Ser. No. 048,136 filed May 15, 1987 discloses 6-substituted compounds of the above general formula wherein R* is:

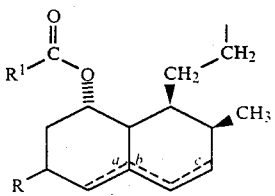

wherein R is $CH_2OH$,

$CO_2R^7$ or

and $R^1$, $R^4$, $R^7$, $R^8$ and $R^9$ are broadly defined organic moieties.

U.S. Pat. Nos. 4,604,472 and 4,733,003 disclose compounds of the above formula wherein R* is:

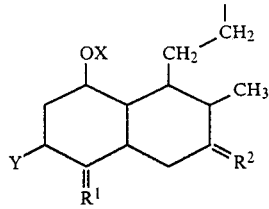

wherein X represents a hydrogen atom or a 2-methylbutyryl group, Y represents a hydrogen atom or a methyl group and $R^1$ and $R^2$ are the same or different and each represents an oxygen atom or a group of formula $=N-OR^3$ where $R^3$ is a hydrogen or alkyl moiety.

Copending U.S. patent application Ser. Nos. 131,695 filed Dec. 11, 1987 and 161,530, 161,579, and 161,529 filed Feb. 29, 1988 disclosure synthetic schemes directed to the preparation of 6-hydroxymethyl-lovastatin analogs.

DETAILED DESCRIPTION OF THE INVENTION

This invention relates to novel intermediates and novel processes for their preparation where said intermediates are useful in a novel preparation of 5'-oxygenated derivatives (I) of lovastatin and analogs thereof at the 8'-acyl side chain and 6'-position of the polyhydronaphthyl ring. Said derivatives (I) and analogs thereof are useful in treating hypercholesterolemia and are disclosed in copending patent application Ser. No. 213,010 filed June 29, 1988.

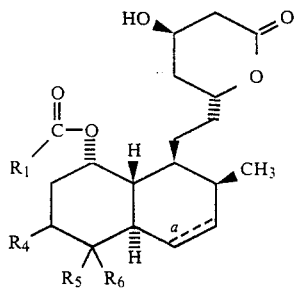

wherein:
$R_1$ is selected from:
(1) $C_{1-10}$ alkyl;
(2) substituted $C_{1-10}$ alkyl in which one or more substituent(s) is selected from
 (a) halogen,
 (b) hydroxy,
 (c) $C_{1-10}$ alkoxy,
 (d) $C_{1-5}$ alkoxycarbonyl,
 (e) $C_{1-5}$ acyloxy,
 (f) $C_{3-8}$ cycloalkyl,
 (g) phenyl,
 (h) substituted phenyl in which the substituents are X and Y,
 (i) $C_{1-10}$ alkylS(0)$_n$ in which n is 0 to 2,
 (j) $C_{3-8}$ cycloalkylS(0)$_n$,
 (k) phenylS(0)$_n$,
 (l) substituted phenylS(0)$_n$ in which the substituents are X and Y, and
 (m) oxo;
(3) $C_{1-10}$ alkoxy;
(4) $C_{2-10}$ alkenyl;
(5) $C_{3-8}$ cycloalkyl;
(6) substituted $C_{3-8}$ cycloalkyl in which one substituent is selected from
 (a) $C_{1-10}$ alkyl
 (b) substituted $C_{1-10}$ alkyl in which the substituent is selected from
  (i) halogen,
  (ii) hydroxy,
  (iii) $C_{1-10}$ alkoxy,
  (iv) $C_{1-5}$ alkoxycarbonyl,
  (v) $C_{1-5}$ acyloxy,
  (vi) phenyl,
  (vii) substituted phenyl in which the substituents are X and Y
  (viii) $C_{1-10}$ alkylS(0)$_n$,
  (ix) $C_{3-8}$ cycloalkylS(0)$_n$,
  (x) phenylS(0)$_n$,
  (xi) substituted phenylS(0)$_n$ in which the substituents are X and Y, and
  (xii) oxo,
 (c) $C_{1-10}$ alkylS(0)$_n$,
 (d) $C_{3-8}$ cycloalkylS(0)$_n$,
 (e) phenylS(0)$_n$,
 (f) substituted phenylS(0)$_n$ in which the substituents are X and Y,
 (g) halogen,
 (h) hydroxy,
 (i) $C_{1-10}$ alkoxy,
 (j) $C_{1-5}$ alkoxycarbonyl,
 (k) $C_{1-5}$ acyloxy,
 (l) phenyl, and
 (m) substituted phenyl in which the substituents are X and Y;
(7) phenyl;
(8) substituted phenyl in which the substituents are X and Y;
(9) amino;
(10) $C_{1-5}$ alkylamino;
(11) di($C_{1-5}$ alkyl)amino;
(12) phenylamino;
(13) substituted phenylamino in which the substituents are X and Y;
(14) phenyl $C_{1-10}$ alkylamino;
(15) substituted phenyl $C_{1-10}$ alkylamino in which the substituents are X and Y;
(16) a member selected from
 (a) piperidinyl,
 (b) pyrrolidinyl,
 (c) piperazinyl,
 (d) morpholinyl, and
 (e) thiomorpholinyl; and
(17) $R_5S$ in which $R_5$ is selected from
 (a) $C_{1-10}$ alkyl,
 (b) phenyl, and
 (c) substituted phenyl in which the substituents are X and Y;

$R_4$ is;
(1) hydrogen;
(2) $C_{1-10}$ alkyl; and
(3) substituted $C_{1-10}$ alkyl in which one or more substituents is selected from
 (a) halogen,
 (b) hydroxy,
 (c) $C_{1-10}$ alkoxy
 (d) $C_{1-5}$ alkoxycarbonyl,
 (e) $C_{1-5}$ alkylacyloxy,
 (f) phenylacyloxy, (g) phenoxycarbonyl,
(h) phenyl $C_{1-5}$ alkylacyloxy,
(i) phenyl $C_{1-5}$ alkoxy,
(j) amino,
(k) $C_{1-5}$ alkylamino,
(l) di($C_{1-5}$ alkyl)amino,
(m) phenylamino,
(n) substituted phenylamino in which the substituents are X and Y;
(o) phenyl $C_{1-5}$ alkylamino,
(p) substituted phenyl $C_{1-5}$ alkylamino in which the substituents are X and Y,
(q) $C_{3-8}$ cycloalkyl,
(r) phenyl,
(s) substituted phenyl in which the substituents are X and Y,
(t) phenylS(0)$_n$,
(u) substituted phenyl S(0)$_n$ in which the substituents are X and Y,
(v) phenyl $C_{1-5}$ alkyl S(0)$_n$,
(w) $C_{1-5}$ alkylS(0)$_n$;
(x) phenylaminoacyloxy,
(y) $C_{1-5}$alkylaminoacyloxy,
(z) $C_{1-5}$alkylacylamino,
(aa) di(phenyl$C_{1-5}$alkyl)phosphonyl
(bb) di($C_{1-5}$alkyl)phosphinyl (4) $R_4$ together with the carbon atom to which it is attached represents a $C_{3-8}$ carbocyclic ring;

$R_5$ and $R_6$ independently are H, OH, OR$_7$ or $R_5$ and $R_6$ together with the carbon to which they are attached represent C=O or $R_5$ and $R_6$ together with the carbon to which they are attached represent a carbocyclic ring of 4 to 7 atoms; provided that when $R_5$ is H, $R_6$ is OH or OR$_7$, and when $R_5$ is OH, $R_6$ is H, and when $R_5$ is OR$_7$, $R_6$ is H;

$R_7$ is

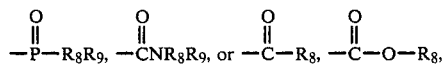

phenyl$C_{1-3}$alkyl, $C_{1-5}$alkyl;

$R_8$ and $R_9$ independently are H, $C_{1-3}$alkyl, phenyl$C_{1-3}$alkyl or aryl wherein aryl is phenyl naphthyl, pyridyl, furanyl, thienyl or phenyl, naphthyl, pyridyl, furanyl or thienyl substituted with groups X and Y provided that when $R_7$ is

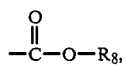

$R_8$ is not H and when $R_7$ is

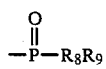

neither $R_8$ nor $R_9$ is H;

X and Y are independently selected from:
(a) OH,
(b) halogen,
(c) trifluoromethyl,
(d) $C_{1-3}$alkoxy,
(e) $C_{1-3}$alkylcarbonyloxy,
(f) phenylcarbonyloxy,
(g) $C_{1-3}$alkyoxycarbonyl,
(h) phenyloxycarbonyl,
(i) hydrogen;
(j) $C_{1-5}$alkyl;

a is a single bond or a double bond.

The 5-oxygenated derivatives of formula (I) are prepared as shown in Schemes 1 and 2. Scheme 1 provides the basic methodology in the synthesis of the 5-oxygenated derivatives when the 3,4-bond in the polyhydronaphthyl ring is saturated, and Scheme 2 describes a modification to incorporate unsaturation in the 3,4-bond.

SCHEME 1

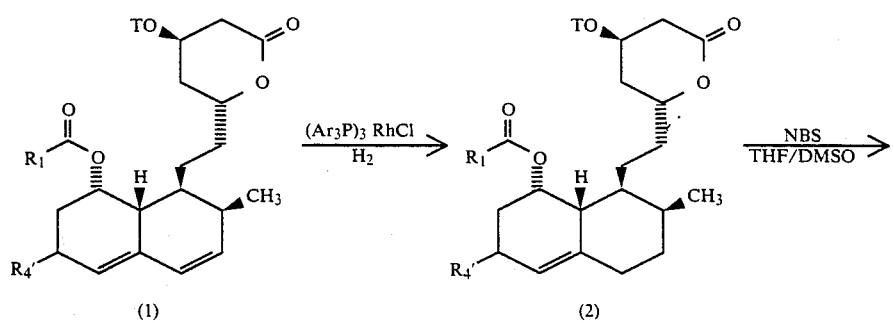

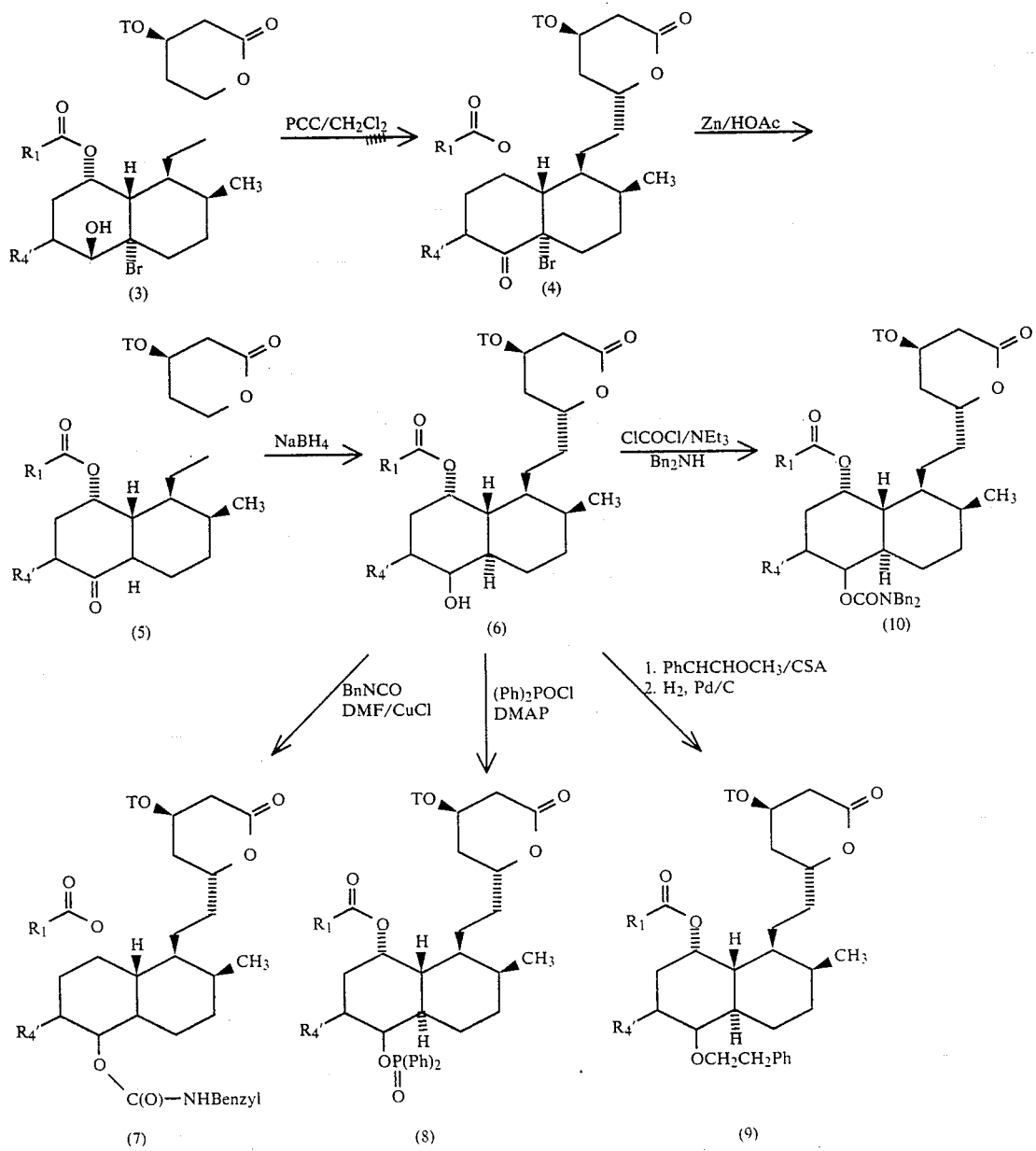
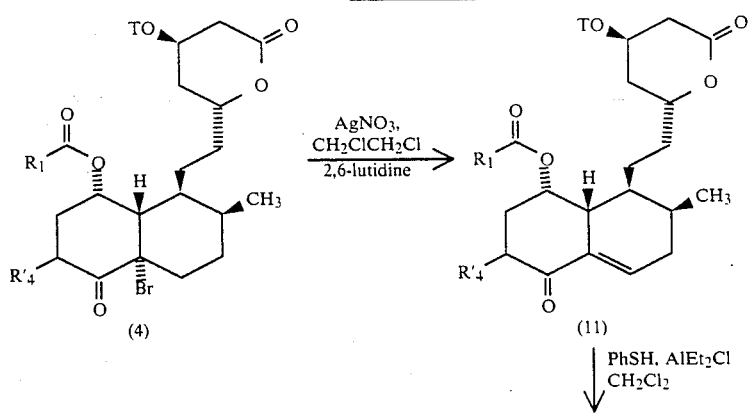

SCHEME 2

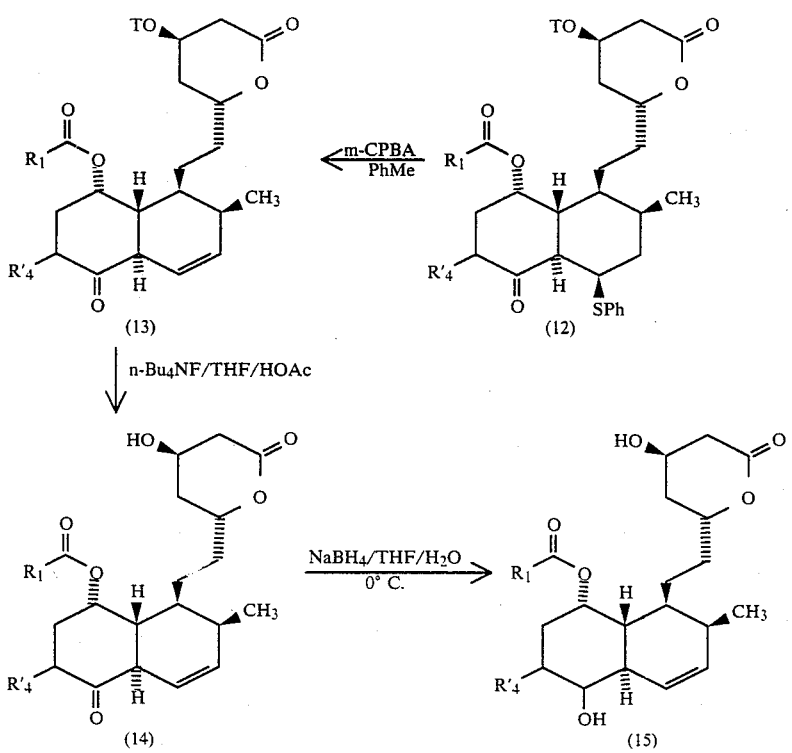

One embodiment of this invention is the compounds of formula (3):

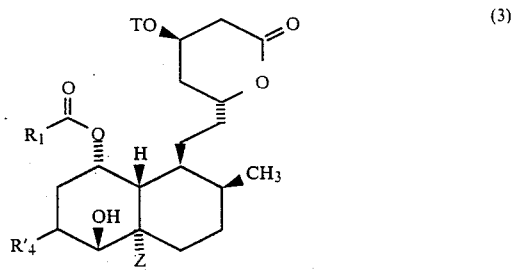

wherein:
Z is Cl or Br; T is H, tert-butyldimethylsilyl, tert-butyldiphenylsilyl, trimethylsilyl, triethylsilyl, triiospropylsilyl, or tetrahydropyranyl;
$R_1$ is selected from:
(1) $C_{1-10}$ alkyl;
(2) substituted $C_{1-10}$ alkyl in which one or more substituent(s) is selected from
  (a) halogen,
  (b) hydroxy,
  (c) $C_{1-10}$ alkoxy,
  (d) $C_{1-5}$ alkoxycarbonyl,
  (e) $C_{1-5}$ acyloxy,
  (f) $C_{3-8}$ cycloalkyl,
  (g) phenyl,
  (h) substituted phenyl in which the substituents are X and Y,
  (i) $C_{1-10}$ alkylS(O)$_n$ in which n is 0 to 2,
  (j) $C_{3-8}$ cycloalkylS(O)$_n$,
  (k) phenylS(O)$_n$,
  (l) substituted phenylS(O)$_n$ in which the substituents are X and Y, and
  (m) oxo;
(3) $C_{1-10}$ alkoxy;
(4) $C_{2-10}$ alkenyl;
(5) $C_{3-8}$ cycloalkyl;
(6) substituted $C_{3-8}$ cycloalkyl in which one substituent is selected from
  (a) $C_{1-10}$ alkyl
  (b) substituted $C_{1-10}$ alkyl in which the substituent is selected from
    (i) halogen,
    (ii) hydroxy,
    (iii) $C_{1-10}$ alkoxy,
    (iv) $C_{1-5}$ alkoxycarbonyl,
    (v) $C_{1-5}$ acyloxy,
    (vi) phenyl,
    (vii) substituted phenyl in which the substituents are X and Y
    (viii) $C_{1-10}$ alkylS(O)$_n$,
    (ix) $C_{3-8}$ cycloalkylS(O)$_n$,
    (x) phenylS(O)$_n$,
    (xi) substituted phenylS(O)$_n$, in which the substituents are X and Y, and
    (xii) oxo,
  (c) $C_{1-10}$ alkylS(O)$_n$,
  (d) $C_{3-8}$ cycloalkylS(O)$_n$,
  (e) phenylS(O)$_n$,
  (f) substituted phenylS(O)$_n$ in which the substituents are X and Y.
  (g) halogen,
  (h) hydroxy,
  (i) $C_{1-10}$ alkoxy,
  (j) $C_{1-5}$ alkoxycarbonyl,
  (k) $C_{1-5}$ acyloxy,
  (l) phenyl, and (m) substituted phenyl in which the substituents are X and Y;
(7) phenyl;
(8) substituted phenyl in which the substituents are X and Y;
(9) amino;
(10) $C_{1-5}$ alkylamino;
(11) di($C_{1-5}$ alkyl)amino;
(12) phenylamino;
(13) substituted phenylamino in which the substituents are X and Y;
(14) phenyl $C_{1-10}$ alkylamino;
(15) substituted phenyl $C_{1-10}$ alkylamino in which the substituents are X and Y;
(16) a member selected from
 (a) piperidinyl,
 (b) pyrrolidinyl,
 (c) piperazinyl,
 (d) morpholinyl, and
 (e) thiomorpholinyl; and
(17) $R_5 S$ in which $R_5$ is selected from
 (a) $C_{1-10}$ alkyl,
 (b) phenyl, and
 (c) substituted phenyl in which the substituents are X and Y;

$R'_4$ is $CH_3$, $CH_2TO$ or H;
X and Y are independently selected from:
 (a) OH,
 (b) halogen,
 (c) trifluoromethyl,
 (d) $C_{1-3}$alkoxy,
 (e) $C_{1-3}$alkylcarbonyloxy,
 (f) phenylcarbonyloxy,
 (g) $C_{1-3}$alkoxycarbonyl,
 (h) phenyloxycarbonyl,
 (i) hydrogen;
 (j) $C_{1-5}$alkyl.

In one class of this embodiment are compounds (3) wherein:
Z is Br;
$R_1$ is selected from:
(1) $C_{1-10}$ alkyl;
(2) substituted $C_{1-10}$ alkyl in which one or more substituent(s) is selected from
 (a) halogen,
 (b) hydroxy,
 (c) $C_{1-10}$ alkoxy,
 (d) $C_{1-5}$ alkoxycarbonyl,
 (e) $C_{1-5}$ acyloxy,
 (f) $C_{3-8}$ cycloalkyl,
 (g) phenyl,
 (h) substituted phenyl in which the substituents are X and Y, and
 (i) oxo;
(3) $C_{3-8}$ cycloalkyl;
(4) substituted $C_{3-8}$ cycloalkyl in which one substituent is selected from
 (a) $C_{1-10}$ alkyl,
 (b) substituted $C_{1-10}$ alkyl in which the substituent is selected from
  (i) halogen,
  (ii) hydroxy,
  (iii) $C_{1-10}$ alkoxy
  (iv) $C_{1-5}$ acyloxy,
  (v) $C_{1-5}$ alkoxycarbonyl,
  (vi) phenyl,
  (vii) substituted phenyl in which the substituents are X and Y, and
  (viii) oxo,
 (c) halogen,
 (d) hydroxy,
 (e) $C_{1-10}$ alkoxy,
 (f) $C_{1-5}$ alkoxycarbonyl,
 (g) $C_{1-5}$ acyloxy,
 (h) phenyl,
 (i) substituted phenyl in which the substituents are X and Y;
 (5) phenylamino;
 (6) substituted phenylamino in which the substituents are X and Y;
 (7) phenyl$C_{1-10}$alkylamino; and
 (8) substituted phenyl $C_{1-10}$ alkylamino in which the substituents are X and Y;

X and Y are independently selected from
 (a) OH,
 (b) F,
 (c) trifluoromethyl,
 (d) $C_{1-3}$alkoxy,
 (e) hydrogen;
 (f) $C_{1-5}$alkyl.

In a subclass are the compounds of formula (3) wherein:
$R_1$ is $C_{1-10}$alkyl;
$R'_4$ is $CH_3$ or $CH_2TO$.

Exemplifying this subclass are the following compounds (2) selected from the group wherein:
(a) $R_1$ is 2-methyl-2-butyl, $R'_4$ is $CH_3$, T is tert-butyldimethylsilyl;
(b) $R_1$ is 2-methyl-2-butyl, $R'_4$ is $CH_2TO$, T is tert-butyldimethylsilyl;
(c) $R_1$ is 2-butyl, $R'_4$ is $CH_3$, T is tert-butyldimethylsilyl;
(d) $R_1$ is 2-butyl, $R'_4$ is $CH_2TO$, T is tert-butyldimethylsilyl.

In a second embodiment is the compounds of formula (4-11)

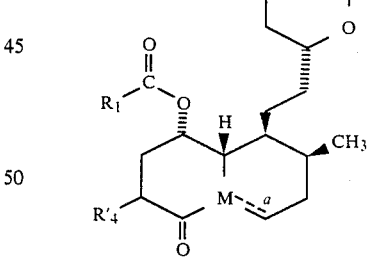
(4-11)

wherein:
M is

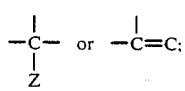

Z is Cl or Br;
T is H, tert-butyldimethylsilyl, tert-butyldiphenylsilyl, trimethylsilyl, triethylsilyl, triiospropylsilyl, or tetrahydropyranyl;
$R_1$ is selected from:
(1) $C_{1-10}$ alkyl;

(2) substituted $C_{1-10}$ alkyl in which one or more substituent(s) is selected from
  (a) halogen,
  (b) hydroxy,
  (c) $C_{1-10}$ alkoxy,
  (d) $C_{1-5}$ alkoxycarbonyl,
  (e) $C_{1-5}$ acyloxy,
  (f) $C_{3-8}$ cycloalkyl,
  (g) phenyl,
  (h) substituted phenyl in which the substituents are X and Y,
  (i) $C_{1-10}$ alkylS(O)$_n$ in which n is 0 to 2,
  (j) $C_{3-8}$ cycloalkylS(O)$_n$,
  (k) phenylS(O)$_n$,
  (l) substituted phenylS(O)$_n$ in which the substituents are X and Y, and
  (m) oxo;
(3) $C_{1-10}$ alkoxy;
(4) $C_{2-10}$ alkenyl;
(5) $C_{3-8}$ cycloalkyl;
(6) substituted $C_{3-8}$ cycloalkyl in which one substituent is selected from
  (a) $C_{1-10}$ alkyl
  (b) substituted $C_{1-10}$ alkyl in which the substituent is selected from
    (i) halogen,
    (ii) hydroxy,
    (iii) $C_{1-10}$ alkoxy,
    (iv) $C_{1-5}$ alkoxycarbonyl,
    (v) $C_{1-5}$ acyloxy,
    (vi) phenyl,
    (vii) substituted phenyl in which the substituted are X and Y
    (viii) $C_{1-10}$ alkylS(O)$_n$,
    (ix) $C_{3-8}$ cycloalkylS(O)$_n$,
    (x) phenylS(O)$_n$,
    (xi) substituted phenylS(O)$_n$ in which the substituents are X and Y, and
    (xii) oxo,
  (c) $C_{1-10}$ alkylS(O)$_n$,
  (d) $C_{3-8}$ cycloalkylS(O)$_n$,
  (e) phenylS(O)$_n$,
  (f) substituted phenylS(O)$_n$ in which the substituents are X and Y,
  (g) halogen,
  (h) hydroxy,
  (i) $C_{1-10}$ alkoxy,
  (j) $C_{1-5}$ alkoxycarbonyl,
  (k) $C_{1-5}$ acyloxy,
  (l) phenyl, and
  (m) substituted phenyl in which the substituents are X and Y;
(7) phenyl;
(8) substituted phenyl in which the substituents are X and Y;
(9) amino;
(10) $C_{1-5}$ alkylamino;
(11) di($C_{1-5}$ alkyl)amino;
(12) phenylamino;
(13) substituted phenylamino in which the substituents are X and Y;
(14) phenyl $C_{1-10}$ alkylamino;
(15) substituted phenyl $C_{1-10}$ alkylamino in which the substituents are X and Y;
(16) a member selected from
  (a) piperidinyl,
  (b) pyrrolidinyl,
  (c) piperazinyl,
  (d) morpholinyl, and
  (e) thiomorpholinyl; and
(17) $R_5S$ in which $R_5$ is selected from
  (a) $C_{1-10}$ alkyl,
  (b) phenyl, and
  (c) substituted phenyl in which the substituents are X and Y;
$R'_4$ is $CH_3$, $CH_2TO$ or H;
X and Y are independently selected from:
  (a) OH,
  (b) halogen,
  (c) trifluoromethyl,
  (d) $C_{1-3}$alkoxy,
  (e) $C_{1-3}$alkylcarbonyloxy,
  (f) phenylcarbonyloxy,
  (g) $C_{1-3}$alkoxycarbonyl,
  (h) phenyloxycarbonyl,
  (i) hydrogen;
  (j) $C_{1-5}$alkyl;
a is a single bond or a double bond provided that when M is C-Z a is a single bond.

In one class of the embodiment of compounds (4-11) are compounds (4) wherein:
M is $$-\underset{Z}{\overset{|}{\underset{|}{C}}}-;$$

Z is Br;
$R_1$ is selected from:
(1) $C_{1-10}$ alkyl;
(2) substituted $C_{1-10}$ alkyl in which one or more substituent(s) is selected from
  (a) halogen,
  (b) hydroxy,
  (c) $C_{1-10}$ alkoxy,
  (d) $C_{1-5}$ alkoxycarbonyl,
  (e) $C_{1-5}$ acyloxy,
  (f) $C_{3-8}$ cycloalkyl,
  (g) phenyl,
  (h) substituted phenyl in which the substituents are X and Y, and
  (i) oxo;
(3) $C_{3-9}$ cycloalkyl;
(4) substituted $C_{3-8}$ cycloalkyl in which one substituent is selected from
  (a) $C_{1-10}$ alkyl,
  (b) substituted $C_{1-10}$ alkyl in which the substituent is selected from
    (i) halogen,
    (ii) hydroxy,
    (iii) $C_{1-10}$ alkoxy
    (iv) $C_{1-5}$ acyloxy,
    (v) $C_{1-5}$ alkoxycarbonyl,
    (vi) phenyl,
    (vii) substituted phenyl in which the substituents are X and Y, and
    (viii) oxo,
  (c) halogen,
  (d) hydroxy,
  (e) $C_{1-10}$ alkoxy,
  (f) $C_{1-5}$ alkoxycarbonyl,
  (g) $C_{1-5}$ acyloxy,
  (h) phenyl, (i) substituted phenyl in which the substituents are X and Y;
(5) phenylamino;
(6) substituted phenylamino in which the substituents are X and Y;
(7) phenyl$C_{1-10}$alkylamino; and
(8) substituted phenyl $C_{1-10}$ alkylamino in which the substituents are X and Y;

X and Y are independently selected from:
(a) OH,
(b) F,
(c) trifluoromethyl,
(d) $C_{1-3}$alkoxy,
(e) hydrogen;
(f) $C_{1-5}$alkyl.

Illustrating this subclass are the compounds of formula (4) wherein:

$R_1$ is $C_{1-10}$alkyl;

$R'_4$ is $CH_3$ or $CH_2TO$.

Exemplifying this subclass are compounds (4) selected from the group wherein:
(a) $R_1$ is 2-methyl-2-butyl, $R'_4$ is $CH_3$, T is tert-butyldimethylsilyl;
(b) $R_1$ is 2-methyl-2-butyl, $R'_4$ is $CH_2TO$, T is tert-butyldimethylsilyl;
(c) $R_1$ is 2-butyl, $R'_4$ is $CH_3$, T is tert-butyldimethylsilyl;
(d) $R_1$ is 2-butyl, $R'_4$ is $CH_2TO$, T is tert-butyldimethylsilyl.

In a second class of the embodiment of compounds (4–11) are compounds (11) wherein:
M is

a is a double bond;
$R_1$ is selected from:
(1) $C_{1-10}$ alkyl;
(2) substituted $C_{1-10}$ alkyl in which one or more substituent(s) is selected from
  (a) halogen,
  (b) hydroxy,
  (c) $C_{1-10}$ alkoxy,
  (d) $C_{1-5}$ alkoxycarbonyl,
  (e) $C_{1-5}$ acyloxy,
  (f) $C_{3-8}$ cycloalkyl,
  (g) phenyl,
  (h) substituted phenyl in which the substituents are X and Y, and
  (i) oxo;
(3) $C_{3-8}$ cycloalkyl;
(4) substituted $C_{3-8}$ cycloalkyl in which one substituent is selected from
  (a) $C_{1-10}$ alkyl,
  (b) substituted $C_{1-10}$ alkyl in which the substituent is selected from
    (i) halogen,
    (ii) hydroxy,
    (iii) $C_{1-10}$ alkoxy
    (iv) $C_{1-5}$ acyloxy,
    (v) $C_{1-5}$ alkoxycarbonyl,
    (vi) phenyl,
  (vii) substituted phenyl in which the substituents are X and Y, and
  (viii) oxo,
(c) halogen,
(d) hydroxy,
(e) $C_{1-10}$ alkoxy,
(f) $C_{1-5}$ alkoxycarbonyl,
(g) $C_{1-5}$ acyloxy,
(h) phenyl,
(i) substituted phenyl in which the substituents are X and Y;
(5) phenylamino;
(6) substituted phenylamino in which the substituents are X and Y;
(7) phenyl$C_{1-10}$alkylamino; and
(8) substituted phenyl $C_{1-10}$ alkylamino in which the substituents are X and Y;

X and Y are independently selected from:
(a) OH,
(b) F,
(c) trifluoromethyl,
(d) $C_{1-3}$alkoxy,
(e) hydrogen;
(f) $C_{1-5}$alkyl.

Illustrating this subclass are the compounds of formula (11) wherein:

$R_1$ is $C_{1-10}$alkyl;

$R'_4$ is $CH_3$ or $CH_2TO$.

Exemplifying this subclass are compounds (11) selected from the group wherein:
(a) $R_1$ is 2-methyl-2-butyl, $R'_4$ is $CH_3$, T is tert-butyldimethylsilyl;
(b) $R_1$ is 2-methyl-2-butyl, $R'_4$ is $CH_2TO$, T is tert-butyldimethylsilyl;
(c) $R_1$ is 2-butyl, $R'_4$ is $CH_3$, T is tert-butyldimethylsilyl;
(d) $R_1$ is 2-butyl, $R'_4$ is $CH_2TO$, T is tert-butyldimethylsilyl.

Intermediates of formula (3) wherein Z is Br are prepared in a process which comprises:
(i) Treating the compound (1)

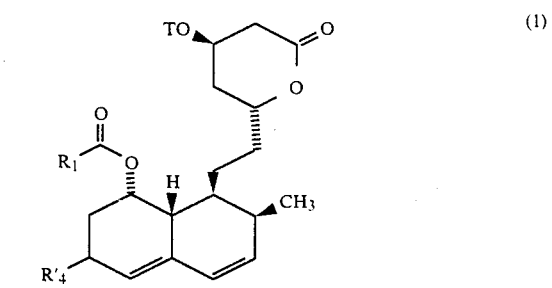

wherein $R_1$, $R'_4$ and T are as defined above with a tris(triarylphosphine)rhodium halide in the presence of hydrogen to form a compound of formula (2);

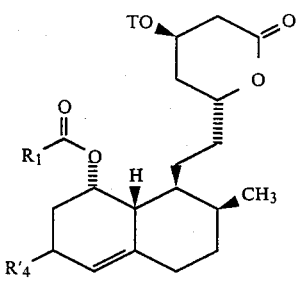

(2)

(ii) treating compound (2) with N-bromosuccimide (NBS) in a mixture of THF/DMSO/H₂O at about 5° C. to yield compound (3).

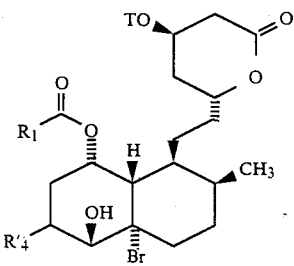

(3)

Intermediates of formula (4) are prepared in a sequence comprising steps (i)–(ii) and further comprising:

(iii) contacting compound (3) with an oxidizing agent such as pyridinium chlorochromate (PCC) to yield compound (4).

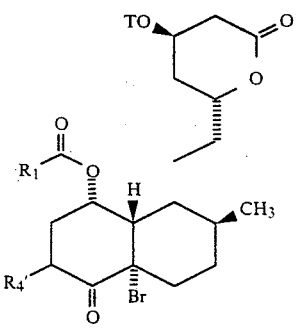

(4)

Intermediates of formula (11) wherein M=—C=C are prepared in a sequence comprising steps (i)–(iii) and further comprising:

(iv) contacting compound (4) under dehydrobrominating conditions such as AgNO₃ in 2,6-lutidine and CH₂ClCH₂Cl to yield a compound (11).

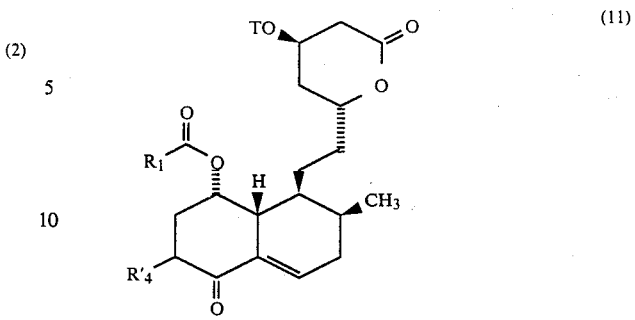

(11)

Compound (2) is prepared from lovastatin by a reduction of the 3,4-double bond following the procedure detailed in copending patent application Ser. No. 092,804, filed Sept. 3, 1987. Where R₄ is 6-hydroxymethyl or a protected hydroxymethyl, the conversion of 6-methyl to 6-hydroxymethyl can be accomplished following the procedure in Ser. No. 048,136, filed May 5, 1987. The hydroxyl group in the lactone ring and at the 6-position of the polyhydronaphthyl ring may be protected (TO) using a silyl protecting group such as tert-butyldimethylsilyl, following the procedure in U.S. Pat. No. 4,444,784. Where the acyl moiety is other than 2-methylbutyryl the acyl group of lovastatin may be hydrolyzed and the hydroxyl group reesterified with an appropriate alkanoyl halide following the procedure in U.S. Pat. No. 4,444,784. The alkanoyl halide can be formed by standard transformations such as substitution with an alkyl moiety or other appropriate electrophile at an acidic C—H site on an available starting material.

Halohydrin (3) may be prepared by anti-addition of HOZ to the double bond employing a N-halosuccimide in H₂O/THF/DMSO, alternatively the addition may be accomplished by the use of HOZ/THF.

The α-haloketone (4) is prepared by oxidation of compound (3) using pyridinium chlorochromate or SO₃/pyridine.

The α-haloketone (4) can be dihydrohalogenated employing an appropriate base in the presence of AgNO₃ to yield the enone compound (11). Illustrative of such bases are triethylamine or collidine.

Compounds of formula (I) may be prepared from intermediates (3), (4) or (10) following the outline in Scheme 1 and 2.

Copending U.S. patent application Ser. No. 092,354 filed Sept. 2, 1987, discloses a method of preparing the 6-α-desmethyl-6-β-methyl lovastatin derivative which can be employed as a starting material in the above scheme. Alternatively, removal of the silyl protecting T of the 6-α-methyl ketone (5) followed by treatment with 1,8-diazabicyclo-[5,4,0] undec-7-ene (DBU) results in the 6β-methyl ketone which after reprotection of the lactone hydroxy group and treatment with NaBH₄ give a mixture of the 6-β-methyl-5(S)-hydroxy compound and the 6-β-methyl-5-(R)-hydroxy compound.

Where the reaction conditions of the above noted chemical transformations would be deleterious to the substituents in the 8-acyloxy moiety, the acetoxy group can be employed as a protecting group which, after the elaboration of the 5-position, can be removed by hydrolysis to give the 8-hydroxy derivative which then an be acylated according to the general procedures described in U.S. Pat. No. 4,661,483.

Where the product formed by the above described synthetic pathways is not the desired form of that compound, then that product may be subjected to one or more further reactions such as hydrolysis, disilylation, salification, esterification, acylation, ammonolysis or lactonizaton by conventional methods.

The following examples illustrate the preparation of intermediates (3), (4) and (10) and the compounds of formulae (I) and (II) and as such are not to be considered as limiting the invention set forth in the claims appended hereto.

EXAMPLE 1

Preparation of 6(R)-[2-[8(S)-(2,2-dimethylbutyryloxy)-2(S)-methyl-5(R)-hydroxy-6(R)-methyl-1,2,3,4,4a(R),5,6,7,8,8a(R)-decahydronaphthyl-1(S)ethyl]-4(R)-hydroxy-3,4,5,6-tetrahydro-2H-pyran-2-one (I-6)

Step 1: Preparation of 6(R)-[2-[8(S)-(2,2-dimethylbutyryloxy)-2(S)-methyl-6(R)-methyl-1,2,3,4,6,7,8,8a(S)-octahydronaphthyl-1(S)ethyl]-4(R)-hydroxy-3,4,5,6-tetrahydro-2H-pyran-2-one (2).

Nitrogen was bubbled through a solution of 50% toluene in absolute ethanol (300 mL) for 5 minutes. Wilkinson's catalyst (5.0 g, 33%/wt.) was added to the solvent and the mixture reduced at room temperature under 50 psi $H_2$ for 1 hour. Simvastatin (1) (15 g, 36 mmol) was added and the resulting pale yellow solution reduced at room temperature under $H_2$ (60 psi) for 40 hours. The mixture was concentrated and the residue heated in toluene (700 mL) at 60° C. in the presence of thiourea (5.0 g, 64 mmol) for 1.5 hours. The mixture was cooled to 0° C. (ice bath), filtered, and concentrated. The residue was diluted with 50% EtOAc/hexane and passed through a pad of silica (~250 cc) to give 2 as a beige solid; mp=128°–129° C. (ethyl acetate/hexane); TLC $R_f$=0.65 (EtOAc); $^1$H NMR* (CDCl$_3$) δ 5.36 (bs, 1H), 5.30 (m, 1H), 4.58 (m,1H), 4.33 (m,1H), 2.68 (dd,J=17 and 5 Hz,1H), 2.68 (m,1H), 2.59 (dd,J=17 and 4 Hz,1H), 2.30–1.20 (m), 1.13 (s,3H), 1.12 (s,3H), 1.05 (d, J=7 Hz,3H), 0.87 (d, J=7 Hz,3H), 0.82 (t, J=7 Hz,3H).

*NMR spectra were measured on a Varian XL-300 spectrometer.

Step 2: Preparation of 6(R)-[2-[8(S)-(2,2-dimethyl butyryloxy)-2(S)-methyl-4a(S)-bromo-5(S)-hydroxy-6(R)-methyl-1,2,3,4,5,6,7,8,8a-(R)-nonahydronaphthyl-1(S)]-ethyl]-4(R)-tert-butyldimethylsilyloxy-3,4,5,6-tetrahydro-2H-pyran-2-one (3)

To a stirred solution of 6(R)-[2-[8(S)-(2,2-dimethyl-butyryloxy)-2(S)-methyl-6(R)-methyl-1,2,3,4,6,7,8,8a(R)-octahydronaphthyl-1(S)]ethyl]-4(R)-tert-butyldimethylsilyloxy-3,4,5,6-tetrahydro-2H-pyran-2-one (95 mg, 0.23 mmol), DMSO (1.0 mL), THF (0.5 mL), and $H_2O$ (12 μL, 0.7 mmol) at 5° C. was added N-bromosuccinimide (NBS) (61 mg, 0.33 mmol). After 1 hour the yellow reaction mixture was diluted with ether, washed with $H_2O$, saturated NaHCO$_3$ and brine, dried (MgSO$_4$), and concentrated. Flash chromatography (silica, 30% EtOAc/hexane) furnished the bromohydrin as a colorless oil.

$^1$H NMR (CDCl$_3$) δ 5.08(m, 1H), 4.54(m, 1H), 4.26(m, 1H), 4.13(d, J=3 Hz, 1H), 2.63–2.48(m, 2H), 2.35–1.1(m), 1.31(d, J=6 Hz, 3H), 1.13(s, 3H), 1.12(s, 3H), 0.87(s, 9H), 0.8(m, 6H) 0.05(s, 3H), 0.04(s,3H).

Step 3: Preparation of 6(R)-[2-[8(S)-(2,2-dimethyl butyryloxy)-2(s)-methyl-4a(S)-bromo-5-oxo-6(R)-methyl-1,2,3,4,5,6,7,8,8a(R)-octahydronaphthyl-1(s)]ethyl]-4(R)-tert-butyldimethylsilyloxy-3,4,5,6-tetrahydro-2H-pyran-2-one(4)

To a stirred mixture of compound 3 (2.4 g, 3.8 mmol), 4A sieves (2.5 g), and dry CH$_2$Cl$_2$ (19 ml) at 0° C. was added pyridinium clorocromate (PCC) (3.2 g, 14.8 mmol). After stirring for 30 minutes, the icebath was removed with continued stirring for 30 minutes. The reaction mixture was diluted with ether and filtered through a celite pad into a filtration flask containing acetic acid (0.8 mL, 14.0 mmol). Concentration at 10° C. gave the crude bromoketone 4. Flash chromatography (silica, 15% EtOAc/hexanes) gave compound 4 as a solid (m.p. 85°–87° C.).

$^1$H NMR (CDCl$_3$) δ 5.24(m,1H), 4.60(m,1H), 4.32 (m,1H), 2.75(m,1H), 2.62(m,2H), 2.40–1.20(m), 1.24(d,J=7 Hz,3H), 1.21(s,3H), 1.19(s,3H), 0.91(s,9H), 0.89(m,6H), 0.11(s,3H), 0.10(s,3H).

Step 4: Preparation of 6(R)-[2-[8(S)-(2,2-dimet hylbutyryloxy)-2(S)-methyl-5-oxo-6(R)-methyl-1,2,3,4,4a(R),6,7,8,8a(R)-nonahydronaphthyl-1(S)ethyl]-4(R)-tert-butyldimethylsilyloxy-3,4,5,6-tetrahydro-2H-pyran-2-one (5)

The crude bromoketone 4 (2.6 g, 3.8 mmol) was dissolved in THF/HOAc (38 mL) followed by treatment with zinc (0.74 g, 11.4 mmol) at ambient temperature. After 1.0 hour of vigorous stirring, the reaction mixture was diluted with ether and the excess zinc removed by filtration. The filtrate was washed with $H_2O$ and brine, dried (MgSO$_4$), and concentrated. Flash chromatography (silica, 15% EtOAc/hexanes) gave compound 5 as a solid (m.p. 147°–148° C.)

$^1$H NMR (CDCl$_3$) δ 5.31 (m, 1H), 4.60(m, 1H), 4.29(m,1H), 2.58(m,2H), 2.24–1.20(m), 1.24(d, J=7 Hz,3H), 1.88(s, 3H), 1.17(s,3H), 0.89(s,9H), 0.87(d, J=7 Hz, 3H), 0.83(t, J=7 Hz,3H), 0.06(s, 6H)

Step 5: Preparation of 6(R)-[2-[8(S)-(2,2-dimeth ylbutyryloxy)-2(S)-methyl-5(R)-hydroxy-6(R)-methyl-1,2,3,4,4a(R),5,6,7,8,8a(R)-decahydronaphthyl-1(S)]ethyl]-4(R)-tert-butyldimethylsilyloxy-3,4,5,6-tetrahydro-2H-pyran-2-one (6)

To a stirred solution of compound 5 (320 mg, 0.58 mmol), THF (2.6 mL), and $H_2O$ (0.3 mL) at 0° C. was added NaBH$_4$ (66 mg, 1.7 mmol). After 35 minutes, the reaction mixture was diluted with ethyl acetate, washed with $H_2O$ (2X) and brine, dried (MgSO$_4$), and concentrated. Flash chromatography (silica, 20% ethyl acetate/hexane) gave compound 6 as a colorless oil.

$^1$H NMR (CDCl$_3$) δ 5.06(m, 1H), 4.60(m, 1H), 4.14(m, 1H), 3.45(dd, J=10 and 5 Hz, 1H), 2.56(m, 2H), 2.15–1.15(m), 1.17(s, 3H), 1.16(s, 3H), 1.07(d, J=7 Hz, 3H), 0.88(s, 9H), 0.88(t, J=7 Hz, 3H), 0.86(d, J=7 Hz, 3H), 0.08(s, 3H), 0.08(s, 3H)

Step 6: Preparation of 6(R)-[2-[8(S)-(2,2-dimethyl-butyryloxy)-2(S)-methyl-5(R)-hydroxy-6(R)-methyl-1,2,3,4,4a(R),6,7,8,8a(R)-decahydronaphthyl-1(S)ethyl]-4(R)-hydroxy-3,4,5,6-tetrahydro-2H-pyran-2-one (I-6)

To a stirred solution of compound 6 (98 mg, 0.18 mmol), THF (530 μL), and HOAc (41 μL, 0.71 mmol) was added tetrabutylammonium fluoride (1M THF, 530 μL, 0.53 mmol) at ambient temperature. After 20 hours, the reaction mixture was diluted with ethyl acetate, washed with $H_2O$ and brine, dried (MgSO$_4$), and concentrated. Flash chromatography (silica, 60% EtOAc/hexane) gave compound (I-6) as a crystalline solid. mp=142°–143° C.

$^1$H NMR (CDCl$_3$) δ 5.05(m, 1H), 4.54(m, 1H), 4.31(m, 1H), 3.42(dd, J=10 and 5 Hz, 1H), 2.69(dd, J=17 and 5 Hz, 1H), 2.57(dd, J=17 and 4 Hz, 1H), 2.12–1.10(m), 1.17(s, 3H), 1.16(s, 3H), 1.06(d, J=7 Hz, 3H), 0.82(t, J=7 Hz, 3H), 0.79(d, J=7 Hz, 3H)
Elemental Anal. $C_{25}H_{42}O_6 \cdot 0.5H_2O$:
Calc'd: C, 67.08; H, 9.68
Found: C, 66.84; H, 9.31

EXAMPLE 2

Preparation of
6(R)-[2-[8(S)-(2,2-dimethylbutyryloxy)-2(S)-methyl-5(R)-benzylaminocarboxy-6(R)-methyl-1,2,3,4,4a(R),5,6,7,8,8a(R)-decahydronaphtyl-1(S)]ethyl]-4(R)-hydroxy-3,4,5,6-tetrahydro-2H-pyran-2-one (I-7)

Step 1: Preparation of 6(R)-[2-[8(S)-(2,2-dimethylbutyryloxy)-2(S)-methyl-6(R)-methyl-1,2,3,4,6,7,8,8a(S)-octahydronaphthyl-1(S)]ethyl]-4-(R)-hydroxy-3,4,5,6-tetrahydro-2H-pyran-2-one (2).

Nitrogen was bubbled through a solution of 50% toluene in absolute ethanol (300 mL) for 5 minutes. Wilkinson's catalyst (5.0 g, 33%/wt.) was added to the solvent and the mixture reduced at room temperature under 50 psi H$_2$ for 1 hour. Simvastatin (15 g, 36 mmol) was added and the resulting pale yellow solution reduced at room temperature under H$_2$ (60 psi) for 40 hours. The mixture was concentrated and the residue heated in toluene (700 mL) at 60° C. in the presence of thiourea (5.0 g, 64 mmol) for 1.5 hours. The mixture was cooled to 0° C. (ice bath), filtered, and concentrated. The residue was diluted with 50% EtOAc/hexane and passed through a pad of silica (~250 cc) to give 2 as a beige solid; mp=128°–129° C. (ethyl/hexane); TLC $R_f$=0.65 (EtOAc); $^1$HNMR (CDCl$_3$) δ 5.36 (bs, 1H), 5.30 (m,1H), 4.58 (m,1H), 4.33 (m,1H), 2.68 (dd,J=17 and 5 Hz,1H), 2.68 (m,1H), 2.59 (dd, J=17 and 4 Hz,1H), 2.30–1.20 (m), 1.13 (s,3H), 1.12 (s,3H), 1.05 (d, J—7 Hz,3H), 0.87 (d, J=7 Hz,3H), 0.82 (t, J=7 Hz,3H).

Step 2: Preparation of 6(R)-[2-[8(S)-(2,2-dimethylbutyryloxy)-2(S)-methyl-4a(S)-bromo-5(S)-hydroxy-6(R)-methyl-1,2,3,4,5,6,7,8,8a -(R)-nonahydronapht-hyl-1(S)]ethyl]-4(R)-tert-butyldimethylsilyloxy-3,4,5,6-tetrahydro-2H-pyran-2-one (3)

To a stirred solution of 6(R)-[2-[8(S)-(2,2-dimethyl-butyryloxy)-2(S)-methyl-6(R)-methyl-1,2,3,4,6,7,8,8a(R)-octahydronaphthyl-1(S)]ethyl]-4(R)-tert-butyldimethylsilyloxy-3,4,5,6-tetrahydro-2H-pyran-2-one (95 mg, 0.23 mmol) DMSO (1.0 mL), THF (0.5 mL), and H$_2$O (12 μL, 0.7 mmol) at 5° C. was added N-bromosuccinimide (NBS) (61 mg, 0.33 mmol). After 1 hour, the yellow reaction mixture was diluted with ether, washed with H$_2$O, saturated NaHCO$_3$ and brine, dried (MgSO$_4$), and concentrated. Flash chromatography (silica, 30% EtOAc/hexane furnished the bromohydrin as a colorless oil.

$^1$H NMR (CDCl$_3$) δ 5.08(m, 1H), 4.54(m, 1H), 4.26(m, 1H), 4.13(d, J=3 Hz,1H), 2.63–2.48(m, 2H), 2.35–1.1(m), 1.31(d, J=6 Hz, 3H), 1.13(s, 3H), 1.12(s, 3H), 0.87(s, 9H), 0.8(m, 6H), 0.05(s, 3H), 0.04(s,3H)

Step 3: Preparation of 6(R)-[2-[8(S)-(2,2-dimethylbutyryloxy)-2(S)-methyl-4-oxo-6(R)-methyl-1,2,3,4,4a(R),6,7,8,8a(R)-nonahydronaphthyl-1(S)]ethyl]-4(R)-tert-butyldimethylsilyloxy-3,4,5,6-tetrahydro-2-H-pyran-2-one (5)

To a stirred mixture of compound 3 (2.4 g, 3.8 mmol), 4A sieves (2.5 g), and dry CH$_2$Cl$_2$ (19 ml) at 0° C. was added pyridinium chlorochromate (PCC) (3.2 g, 5.2 mmol). After stirring for 30 minutes, the icebath was removed with continued stirring for 30 minutes. The reaction mixture was diluted with ether and filtered through a celite pad into a filtration flask containing acetic acid (0.8 mL, 14.0 mmol). Concentration at 10° C. gave the crude bromoketone (4). The crude bromoketone was dissolved in THF/HOAc (38 mL) followed by treatment with zinc (0.74 g, 11.4 mmol) at ambient temperature. After 1.0 hour of vigorous stirring, the reaction mixture was diluted with ether and the excess zinc removed by filtration. The filtrate was washed with H$_2$O and brine, dried (MgSO$_4$), and concentrated. Flash chromatography (silica, 15% EtOAc/hexanes) gave compound 5 as a solid. (m.p. 147°–148° C.)

$^1$NMR (CDCl$_3$) δ 5.31(m, 1H), 4.60(m, 1H), 4.29(m, 1H), 2.58(m, 2H), 2.24–1.20(m), 1.24(d, J=7 Hz, 3H), 1.88(s, 3H), 1.17(s, 3H), 0.89(s, 9H), 0.87(d, J=7 Hz, 3H), 0.83(t, J=7 Hz, 3H), 0.06(s, 6H)

Step 4: Preparation of 6(R)-[2-[8(S)-(2,2-dimethylbutyryloxy)-2(S)-methyl-5(R)-hydroxy-6(R)-methyl-1,2,3,4,4a(R),5,6,7,8,8a(R)-decahydronaphthyl-1(S)]ethyl]-4(R)-tert-butyldimethylsilyloxy-3,4,5,6-tetrahydro-2H-pyran-2-one (6)

To a stirred solution of compound 5 (320 mg, 0.58 mmol), THF (2.6 mL), and H$_2$O (0.3 mL) at 0° C. was added NaBH$_4$ (66 mg, 1.7 mmol). After 35 minutes, the reaction mixture was diluted with ethyl acetate, washed with H$_2$O (2X) and brine, dried (MgSO$_4$), and concentrated. Flash chromatography (silica, 20% ethyl acetate/hexane) gave compound 6 as a colorless oil.

$^1$NMR (CDCl$_3$) δ 5.06(m, 1H), 4.60(m, 1H), 4.14(m, 1H), 3.45(dd, J=10 and 5 Hz, 1H), 2.56(m, 2H), 2.15–1.15(m), 1.17(s, 3H), 1.16(s, 3H), 1.07(d, J=7 Hz, 3H), 0.88(s, 9H), 0.88(t, J=7 Hz, 3H), 0.86(d, J=7 Hz, 3H), 0.08(s, 3H), 0.08(s, 3H)

Step 5: Preparation of 6(R)-[2-[8(S)-(2,2-dimethylbutyryloxy)-2(S)-methyl-5(R)-benzylaminocarbonyloxy-6(R)-methyl-1,2,3,4,4a(R),5,6 7,8,8a(R)-decahydronaphthyl-1(S)]ethyl]-4-(R)-tert-butyldimethylsilyloxy-3,4,5,7-tetrahydro-2H-pyran-2H-one (7)

To a mixture of compound 6 (227 mg, 0.41 mmol), degassed DMF (2.0 mL), and CuCl (41 mg, 0.41 mmol) at 25° C. was added benzyl isocyanate (82 mg, 0.62 mmol). After 1 hour, the dark green mixture was diluted with ether, washed with H$_2$O and brine, dried (MgSO$_4$), and concentrated. Flash chromatography (silica, 20% EtOAc/hexane) furnished compound 7 as a colorless oil.

$^1$H NMR (CDCl$_3$) δ 7.30(m, 5H), 5.06(m, 1H), 4.93(m, 1H), 4.61(dd, J=10 and 5 Hz, 1H), 4.37(d, J=6 Hz, 2H), 4.25(m, 1H), 2.55(m, 2H), 2.27(m, 1H), 2.00–1.10(m), 1.14(s, 3H), 1.13(s, 3H), 0.86(s, 9H), 0.80(m, 9H), 0.06(s, 6H).

Step 5: Preparation of 6(R)-[2-[8(S)-(2,2-dimethylbutyryloxy)-2(S)-methyl-5(R)-benzylaminocarbonyloxy-6(R)-methyl-1,2,3,4,4a(R),5,6, 7,8,8a(R)-decahydronaphthyl-1(S)]ethyl]-4(R)-hydroxy-3,4,5,6-tetrahydro-2H-pyran-2-one (I-7)

Utilizing the same procedure of Example 1, Step 5, the compound 7 (80 mg, 0.11 mmol) was converted to the desired compound (I-7) which was an amorphous solid.

$^1$H NMR (CDCl$_3$) δ 7.30(m, 5H), 5.08(m, 1H), 5.02(t, J=6 Hz, 1H), 4.59(dd, J=10 and 5 Hz, 1H), 4.54(m, 1H), 4.34(d, J=6 Hz, 1H), 4.30(m, 1H), 3.03(bs, 1H), 2.69(dd, J=18 and 5 Hz, 1H), 2.58(dd, J=18 and 4 Hz, 1H), 2.26(m, 1H), 2.00–1.10(m), 1.14(s, 3H), 1.13(s, 3H), 0.82(t, J=7 Hz, 3H), 0.78(d, J=7 Hz, 3H).
Elemental Anal. $C_{33}H_{49}O_7N \cdot 1.5H_2O$ Calc'd: C, 66.20; H, 8.75 N, 2.34
Found: C, 65.86; H, 8.99 N, 2.03

EXAMPLE 3

Preparation of
6(R)-[2-[8(S)-(2,2-dimethylbutyryloxy)-2(S)-methyl-5(R)-(1-phenylethyl-2-oxy)-6(R)-methyl-1,2,3,4,4a(R),5,6,7,8,8a(R)-decahydronaphthyl-1(S)]-ethyl]-4(R)-hydroxy-3,4,5,6-tetrahydro-2H-pyran-2-one (I-9)

Example 1, Steps 1–4 were repeated but substituting tert-butyldiphenylsilyl as the hydroxy protecting group.

Step 5: 6(R)-[2-[8(S)-(2,2-dimethylbutyryloxy)-2(S)-methyl-5(R)-(1-phenylethylen-2-oxy)-6(R)-methyl-1,2,3,4,4a(R),5,6,7,8,8a(R)-decahydronaphthyl-1(S)]ethyl]-4(R)-tert-butyldiphenylsilyloxy-3,4,5,6-tetrahydro-2H-pyran-2-one (9a)

To a stirred solution of 6(R)-[2-[8(S)-(2,2-dimethylbutyryloxy)-2(S)-methyl-5(R)-hydroxy-6(R)-methyl-1,2,3,4,4a(R),5,6,7,8,8a(R)-decahydronaphthyl-1(S)ethyl]-4(R)-tert-butyldiphenylsilyloxy-3,4,5,6-tetrahydro-2H-pyran-2-one (270 mg, 0.40 mmol), β-methoxystyrene (165 μL, 1.2 mmol) and dry CH$_2$Cl$_2$ (4 mL) at 0° C. was added (±)-camphorsulfonic acid (23 mg, 0.10 mmol). After 15 minutes, the cooling bath was removed and stirring continued for 3 hours. The reaction was quenched with NEt$_3$ (195 μL, 1.2 mmol) concentrated, and the residue subjected to flash chromatography (silica, 15% EtOAc/hexane) to afford compound 9a as a colorless foam.

$^1$H NMR (CDCl$_3$) δ 7.68–7.20(m, 15H), 6.23(d, J=7 Hz, 1H). 5.20(d, J=7 Hz, 1H), 5.09(m, 1H), 4.67(m, 1H), 4.27(m, 1H), 3.56(dd, J=10 and 5 Hz, 1H), 2.57(m, 1H), 2.43(dd, J=18 and 4 Hz, 1H), 2.26(m, 1H), 2.10–1.10(m), 1.17(s, 3H), 1.16(s, 3H), 1.08(s, 9H), 0.86(t, J=7 Hz, 3H), 0.84(d, J=7 Hz, 3H)

Step 5: Preparation of 6(R)-[2-[8(S)-(2,2-dimethylbutyryloxy)-2(S)-methyl-5(R)-(1-phenylethyl-2-oxy)-6(R)-methyl-1,2,3,4,4a(R),5,6,7,8a(R)-decahydronapht-hyl-1(S)]ethyl]-4(R)-tetrabutyldiphenylsilyloxy-3,4,5,6-tetrahydro-2H-pyran-2-one (9).

A mixture of compound 9a (150 mg, 0.19 mmol) 10% Pd/C (30 mg), and ethyl acetate (5.0 ml) was stirred at 25° C. under a hydrogen atmosphere (1 atm) for 8.0 hours. The reaction mixture was filtered through a celite pad and concentrated. Flash chromatography (silica, 15% ethyl acetate/hexane) gave compound 9 as a colorless oil. $^1$H NMR (CDCl$_3$) δ 7.65–7.20(m, 15H), 5.00(m, 1H), 4.66 (m, 1H), 4.23(m, 1H), 3.78(m, 1H), 3.46 (m, 1H), 3.02(dd, J=10 and 5 Hz, 1H), 2.88(ddd, J=7,7, and 3 Hz, 2H), 2.56(m, 1H), 2.41(dd, J=18 and 4 Hz, 1H), 2.22(m, 1H), 2.05–1.10(m), 1.14(s, 3H), 1.08(s,9H), 0.98(d, J=7 Hz, 3H), 0.82(t, J=7 Hz, 3H), 0.79(d, J=7 Hz, 3H).

Step 6: Preparation of 6(R)-[2-[8(S)-(2,2-dimethylbutryloxy)-2(S)-methyl-5(R)-(1-phenylethyl-2-oxy)-6(R)-methyl-1,2,3,4,4a(R),5,6,7,8, 8a(R)-decahydronaphthyl-1(S)]ethyl]-4(R)-hydroxy-3,4,5,6-tetrahydro-2H-pyran-2-one (I-9)

Utilizing the procedure of Example 1, Step 5 the compound 9 (39 mg, 50 mmol) was converted to the desired compound I-9 which was a colorless oil.

$^1$H NMR (CDCl$_3$) δ 7.25(m, 5H), 5.05(m, 1H), 4.55(m, 1H), 4.32(m, 1H), 3.73(m, 1H), 3.47 (m, 1H), 3.01(dd, J=10 and 5 Hz, 1H), 2.88(m, 2H), 2.71(dd, J=18 and 5 Hz, 1H), 2.59 (dd, J=18 and 4 Hz, 1H), 2.22(m, 2H), 2.00–1.10(m), 1.14(s, 3H), 1.13(s, 3H), 0.99 (d, J=7 Hz, 3H), 0.82(t, J=7 Hz, 3H), 0.78(d, J=7 Hz,3H).

Elemental Analysis: C$_{33}$H$_{50}$O$_6$.0.25 H$_2$O
Calc'd: C, 72.43; H, 9.32
Found: C, 72.53; H, 9.32

EXAMPLE 5

Preparation of
6(R)-[2-[8(S)-(2,2-dimethylbutyryloxyl)-2(S)-methyl-5(R)-dibenzylaminocarbonyloxy-6(R)-methyl-1,2,3,4,4a(R),5,6,7,8,8a(R)-decahydronaphthyl-1(S)ethyl]-4(R)-hydroxy-3,4,5,6,-tetrahydro-2H-pyran-2-one (I-10)

Example 1, Steps 1–4 were repeated but substituting tert-butyldiphenylsilyl as the hydroxy protecting group.

Step 4: Preparation of 6(R)-[2-[8(S)-(2,2-dimethylbutyryloxy)-2(S)-methyl-5(R)-dibenzylaminocarbonyloxy-6(R)-methyl-1,2,3,4,4a(R),5,6, 7,8,8a(R)-decahydronaphthyl-1(S)]ethyl]-4(R) tert-butyldiphenylsilyloxy-3,4,5,6-tetrahydro-2H-pyran-2-one (10).

A solution of 6(R)-[2-[8(S)-(2,2-dimethylbutryloxy)-2(S)-methyl-5(R)-hydroxy-6(R)-methyl-1,2,3, 4,4a(R),5,6,7,8,8a(R)-decahydronaphthyl-1(S)]ethyl]-4(R)-tert-butyldiphenylsilyloxy-3,4,5,6-tetrahydro-2H-pyran-2-one (25 mg, 37 mmol), triethylamine (21 μL, 0.15 mmol), and dry CH$_2$Cl$_2$ (200 μL) was added dropwise to a stirred solution of phosgene (20% in toluene, 67 μL, 0.15 mmol) and CH$_2$Cl$_2$ (600 μL) at 0° C. After 5 minutes the cooling bath was removed and the reaction mixture stirred for 20 minutes. Concentration in situ followed by sequential addition of CH$_2$Cl$_2$ (400 μL) and dibenzylamine (8 μL, 41 mmol) at ambient temperature resulted in a heterogeneous mixture. After 15 minutes the reaction mixture was diluted with ether, washed with H$_2$O and brine, dried (MgSO$_4$), and concentrated. Flash chromatography (silica, 15–20% ethyl acetate/hexane) gave compound 10 as an oil.

$^1$H NMR (CDCl$_3$) δ 7.63–7.26(m, 20H), 5.12(m, 1H), 4.75(dd, J=10 and 5 Hz, 1H), 4.60(m, 1H), 4.40 (m, 2H), 4.33(m, 1H), 2.60(m, 2H), 2.20–1.10(m), 1.17(s, 3H), 1.16(s, 3H), 1.07(s, 9H), 1.00 (d, J=7 Hz, 3H), 0.80(m, 6H).

Step 5: Preparation of 6(R)-[2-[8(S)-(2,2-dimethylbutyryloxyl)-2(S)-methyl-5(R)-dibenzylaminocarbonyloxy-6(R)-methyl-1,2,3,4,4a(R),5,6,7, 8,8a(R)-decahydronaphthyl-1(S)]ethyl]-4(R)-hydroxy-3,4,5,6-tetrahydro-2H-pyran-2-one (I-10).

Compound 10 (72 mg, 79 mmol) was dissolved in a premixed solution of tetrabutylammonium flouride (1M in THF, 300 μL, 0.3 mmol), HOAc (20 mL, 0.3 mmol), and THF (300 μL) followed by heating at 50° C. for 1.0 our. The cooled reaction mixture was diluted with ether, washed with H$_2$O and brine, dried (MgSO$_4$), and concentrated. Flash chromatography (silica, 60% EtOAc/hexane) gave compound I-10 as a colorless foam.

$^1$H NMR (CDCl$_3$) δ 7.37–7.18(m, 10H), 5.11(m, 1H), 4.75(dd, J=10 and 5 Hz, 1H), 4.59(m, 1H), 4.47 (m, 3H), 4.34(m, 1H), 2.72(dd, J=18 and 5 Hz, 1H),2.61(dd, J=18 and 3 Hz, 1H), 2.32(m, 1H), 2.00–1.10(m), 1.16(s, 3H), 1.15(s, 3H), 1.00(d, J=7 Hz, 3H), 0.84(t, J=7 Hz, 3H), 0.83(d, J=7 Hz, 3H).

Elemental Analysis: C$_{40}$H$_{55}$O$_7$N.0.5 H$_2$O
Calc'd: C, 71.61; H, 8.41; N, 2.09
Found: C, 71.66; H, 8.31; N, 2.04

EXAMPLE 6

Preparation of 6(R)-[2-[8(S)-(2,2-dimethylbutyryloxy)-2(S)-methyl-5(R)-diphenylphosphinyloxy-6(R)-methyl-1,2,3,4,4a(R),5,6,7,8,8a(R)-decahydronaphthyl-1(S)]ethyl]-4(R)-hydroxy-3,4,5,6-tetrahydro-2H-pyran-2-one (I-8)

Example 1, Steps 1–4 were repeated but substituting tert-butyldiphenylsilyl as the hydroxyl protecting group.

Step 4: Preparation of 6(R)-[2-[8(S)-(2,2-dimethylbutyryloxy)-2(S)-methyl-5(R)-diphenylphosphinyloxy-6(R)-methyl-1,2,3,4,4a(R),5,6, 7,8,8a(R)-decahydronaphthyl-1(S)]ethyl]-4(R)-tert-butyldiphenylsilyloxy-3,4,5,6,-tetrahydro-2H-pyran-2-one (8).

To a stirred solution of 6(R)-[2-[8(S)-(2,2-dimethylbutyryloxy)-2(S)-methyl-5(R)-hydroxy-6(R)-methyl-1,2,3,4,4a(R),5,6,7,8,8a(R)-decahydronaphthyl-1(S)]ethyl]-4(R)-tert-butyldiphenylsilyloxy-3,4,5,6-tetrahydro-2H-pyran-2-one (59 mg, 87 μmol) N,N-dimethyl aminopyridine (DMAP) (43 mg, 0.35 mmol), and CH₂Cl₂ (0.44 mL) at ambient temperature was added diphenyl phosphinic chloride (33 μL, 0.17 mmol). After 20 minutes the reaction mixture was diluted with ether, washed with H₂O and brine, dried (MgSO₄), and concentrated. Flash chromatography (silica, 45% EtOAc/hexane) gave compound 8 as an oil.

$^1$H NMR (CDCl₃) δ 7.85–7.25(m, 20H), 4.98(m, 1H), 4.64(m, 1H), 4.28(m, 2H), 2.55(m, 1H), 2.39(dd, J=18 and 4 Hz, 1H), 2.05–1.10(m), 1.14(s, 3H),1.13(s, 3H), 1.12(d, J=7 Hz, 3H), 1.03(s, 9H), 0.81(t, J=7 Hz, 3H), 0.73(d, J=7HZ, 3H).

Step 5: Preparation of 6(R)-[2-[8(S)-(2,2-dimethylbutyryloxy)-2(S)-methyl-5(R)-diphenylphosphinyloxy-6(R)-methyl-1,2,3,4,4a(R),5,6,7,8, 8a(R)-decahydronaphthyl-1(S)]ethyl]-4(R)-hydroxy-3,4,5,6-tetrahydro-2H-pyran-2-one (I-8)

To a stirred solution of compound 8 (64 mg 73 μmol), THF (0.3 mL), and HOAc (17 μL, 0.3 mmol) was added tetrabutylammonium fluoride (1M in THF, 300 μL, 0.3 mmol) followed by heating at 50° C. After 3.0 hours the cooled reaction mixture was diluted with ether, washed with H₂O and brine, dried (MgSO₄), and concentrated. Flash chromatography (silica, 80% ethyl acetate/hexane) gave compound (I-8) as a colorless oil.

$^1$H NMR (CDCl₃) δ 7.80(m, 4H) 7.46(m, 6H), 5.01(m, 1H), 4.54(m, 1H), 4.30(m, 1H), 4.27(m, 1H), 2.62(m, 3H), 2.10–1.10(m), 1.14(s, 3H), 1.13(s, 3H), 1.12 (d, J=7 Hz, 3H), 0.82(t, J=7 Hz, 3H), 0.73(d, J=7 Hz, 3H).
Elemental Analysis: C₃₇H₅₁O₇P.0.5 H₂O
Calc'd: C, 68.60; H, 8.09
Found: c, 68.69; H, 8.03

EXAMPLE 7

Preparation of 6(R)-[2-[8(S)-(2,2-dimethylbutyryloxy)-2(S)-methyl-5-oxo-6(R)-methyl-1,2,3,6,7,8,8a(R)-heptahydronaphthyl-1(S)]-ethyl]-4(R)-tert-butyldimethylsilyloxy-3,4,5,6-tetrahydro-2H-pyran-1-one (11)

A mixture of the bromoketone 4, (50 mg, 79 μmol), from Example 1, step 3, 1,2-dichloroethane (1.0 mL), and 2,6-lutidine (17 μL, 150 mmol) at 25° C. was treated with AgNO₃(25 mg, 150 mmol). After 2.0 hours the heterogeneous mixture was diluted with ether, washed with H₂O and brine, dried (MgSO₄), and concentrated.

Flash chromataography (silica, 15% EtOAc/hexanes) gave compound 11 as an oil.

$^1$H NMR (CDCl₃) δ 6.77 (m,1H), 5.40(m,1H), 4.62 (m,1H), 4.31(m,1H) 2.75–1.10(m), 1.15 (d,J=7 Hz, 3H), 1.13(s,3H), 0.91(s,9H), 0.81(t,J=7 Hz, 3H), 0.79 (d,J=7 Hz,3H), 0.10(s,6H).

What is claimed is:

1. A compound of structural formula (3):

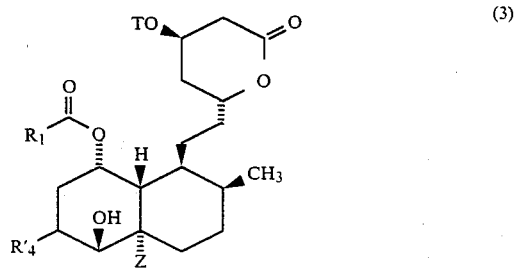

wherein:

Z is Cl or Br;

T is H, tert-butyldimethylsilyl, tert-butyldiphenylsilyl, trimethylsilyl, triethylsilyl, triiosopropylsilyl, or tetrahydropyranyl;

R₁ is selected from:
  (1) C₁₋₁₀ alkyl;
  (2) substituted C₁₋₁₀ alkyl in which one or more substituent(s) is selected from
     (a) halogen,
     (b) hydroxy,
     (c) C₁₋₁₀ alkoxy,
     (d) C₁₋₅ alkoxycarbonyl,
     (e) C₁₋₅ acyloxy,
     (f) C₃₋₈ cycloalkyl,
     (g) phenyl,
     (h) substituted phenyl in which the substituents are X and Y,
     (i) C₁₋₁₀ alkylS(O)$_n$ in which n is 0 to 2,
     (j) C₃₋₈ cycloalkylS(O)$_n$,
     (k) phenylS(O)$_n$,
     (l) substituted phenylS(O)$_n$ in which the substituents are X and Y, and
     (m) oxo;
  (3) C₁₋₁₀ alkoxy;
  (4) C₂₋₁₀ alkenyl;
  (5) C₃₋₈ cycloalkyl;
  (6) substituted C₃₋₈ cycloalkyl in which one substituent is selected from
     (a) C₁₋₁₀ alkyl
     (b) substituted C₁₋₁₀ alkyl in which the substituent is selected from
        (i) halogen,
        (ii) hydroxy,
        (iii) C₁₋₁₀ alkoxy,
        (iv) C₁₋₅ alkoxycarbonyl,
        (v) C₁₋₅ acyloxy,
        (vi) phenyl,
        (vii) substituted phenyl in which the substituents are X and Y
        (viii) C₁₋₁₀ alkylS(O)$_n$,
        (ix) C₃₋₈ cycloalkylS(O)$_n$,
        (x) phenylS(O)$_n$,
        (xi) substituted phenylS(O)$_n$ in which the substituents are X and Y, and
        (xii) oxo,
     (c) C₁₋₁₀ alkylS(O)$_n$, (d) $C_{3-8}$ cycloalkylS(O)$_n$,
(e) phenylS(O)$_n$,
(f) substituted phenylS(O)$_n$ in which the substituents are X and Y,
(g) halogen,
(h) hydroxy,
(i) $C_{1-10}$ alkoxy,
(j) $C_{1-5}$ alkoxycarbonyl,
(k) $C_{1-5}$ acyloxy,
(l) phenyl, and
(m) substituted phenyl in which the substituents are X and Y;
(7) phenyl;
(8) substituted phenyl in which the substituents are X and Y;
(9) amino;
(10) $C_{1-5}$ alkylamino;
(11) di($C_{1-5}$ alkyl)amino;
(12) phenylamino;
(13) substituted phenylamino in which the substituents are X and Y;
(14) phenyl $C_{1-10}$ alkylamino;
(15) substituted phenyl $C_{1-10}$ alkylamino in which the substituents are X and Y;
(16) a member selected from
 (a) piperidinyl,
 (b) pyrrolidinyl,
 (c) piperazinyl,
 (d) morpholinyl, and
 (e) thiomorpholinyl; and
(17) R$_5$S in which R$_5$ is selected from
 (a) $C_{1-10}$ alkyl,
 (b) phenyl, and
 (c) substituted phenyl in which the substituents are X and Y;
R'$_4$ is CH$_3$, CH$_2$TO or H;
X and Y are independently selected from:
(a) OH,
(b) halogen,
(c) trifluoromethyl,
(d) $C_{1-3}$alkoxy,
(e) $C_{1-3}$alkylcarbonyloxy,
(f) phenylcarbonyloxy,
(g) $C_{1-3}$alkoxycarbonyl,
(h) phenyloxycarbonyl,
(i) hydrogen;
(j) $C_{1-5}$alkyl.

2. A compound according to claim 1 wherein:
Z is Br;
R$_1$ is selected from:
(1) $C_{1-10}$ alkyl;
(2) substituted $C_{1-10}$ alkyl in which one or more substituent(s) is selected from
 (a) halogen,
 (b) hydroxy,
 (c) $C_{1-10}$ alkoxy,
 (d) $C_{1-5}$ alkoxycarbonyl,
 (e) $C_{1-5}$ acyloxy,
 (f) $C_{3-8}$ cycloalkyl,
 (g) phenyl,
 (h) substituted phenyl in which the substituents are X and Y, and
 (i) oxo;
(3) $C_{3-8}$ cycloalkyl;
(4) substituted $C_{3-8}$ cycloalkyl in which one substituent is selected from
 (a) $C_{1-10}$ alkyl,
 (b) substituted $C_{1-10}$ alkyl in which the substituent is selected from
  (i) halogen,
  (ii) hydroxy,
  (iii) $C_{1-10}$ alkoxy
  (iv) $C_{1-5}$ acyloxy,
  (v) $C_{1-5}$ alkoxycarbonyl,
  (vi) phenyl,
  (vii) substituted phenyl in which the substituents are X and Y, and
  (viii) oxo,
 (c) halogen,
 (d) hydroxy,
 (e) $C_{1-10}$ alkoxy,
 (f) $C_{1-5}$ alkoxycarbonyl,
 (g) $C_{1-5}$ acyloxy,
 (h) phenyl,
 (i) substituted phenyl in which the substituents are X and Y;
(5) phenylamino;
(6) substituted phenylamino in which the substituents are X and Y;
(7) phenyl$C_{1-10}$alkylamino; and
(8) substituted phenyl $C_{1-10}$ alkylamino in which the substituents are X and Y;
X and Y are independently selected from
(a) OH,
(b) F,
(c) trifluoromethyl,
(d) $C_{1-3}$alkoxy,
(e) hydrogen;
(f) $C_{1-5}$alkyl.

3. A compound according to claim 2 wherein:
R$_2$ is $C_{1-10}$alkyl;
R'$_4$ is CH$_3$ or CH$_2$TO.

4. A compound according to claim 3 selected from the group wherein:
(a) R$_1$ is 2-methyl-2-butyl, R'$_4$ is CH$_3$, T is tert-butyldimethylsilyl;
(b) R$_1$ is 2-methyl-2-butyl, R'$_4$ is CH$_2$TO, T is tert-butyldimethylsilyl;
(c) R$_1$ is 2-butyl, R'$_4$ is CH$_3$, T is tert-butyldimethylsilyl;
(d) R$_1$ is 2-butyl, R'$_4$ is CH$_2$TO, T is tert-butyldimethylsilyl, 5. A compound of structural formula (4-11):

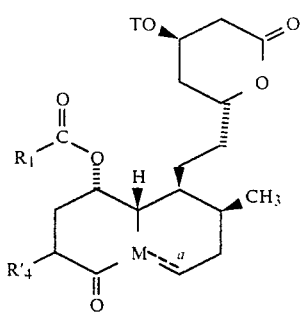

(4-11)

wherein:
M is

Z is Cl or Br;
T is H, tert-butyldimethylsilyl, tert-butyldiphenylsilyl, trimethylsilyl, triethylsilyl, triiospropylsilyl, or tetrahydropyranyl;
$R_1$ is selected from:
(1) $C_{1-10}$ alkyl;
(2) substituted $C_{1-10}$ alkyl in which one or more substituent(s) is selected from
  (a) halogen,
  (b) hydroxy,
  (c) $C_{1-10}$ alkoxy,
  (d) $C_{1-5}$ alkoxycarbonyl,
  (e) $C_{1-5}$ acyloxy,
  (f) $C_{3-8}$ cycloalkyl,
  (g) phenyl,
  (h) substituted phenyl in which the substituents are X and Y,
  (i) $C_{1-10}$ alkylS(O)$_n$ in which n is 0 to 2,
  (j) $C_{3-8}$ cycloalkylS(O)$_n$,
  (k) phenylS(O)$_n$,
  (l) substituted phenylS(O)$_n$ in which the substituents are X and Y, and
  (m) oxo;
(3) $C_{1-10}$ alkoxy;
(4) $C_{2-10}$ alkenyl;
(5) $C_{3-8}$ cycloalkyl;
(6) substituted $C_{3-8}$ cycloalkyl in which one substituent is selected from
  (a) $C_{1-10}$ alkyl
  (b) substituted $C_{1-10}$ alkyl in which the substituent is selected from
    (i) halogen,
    (ii) hydroxy,
    (iii) $C_{1-10}$ alkoxy,
    (iv) $C_{1-5}$ alkoxycarbonyl,
    (v) $C_{1-5}$ acyloxy,
    (vi) phenyl,
    (vii) substituted phenyl in which the substituents are X and Y
    (viii) $C_{1-10}$ alkylS(O)$_n$,
    (ix) $C_{3-8}$ cycloalkylS(O)$_n$,
    (x) phenylS(O)$_n$,
    (xi) substituted phenylS(O)$_n$ in which the substituents are X and Y, and
    (xii) oxo,
  (c) $C_{1-10}$ alkylS(O)$_n$,
  (d) $C_{3-8}$ cycloalkylS(O)$_n$,
  (e) phenylS(O)$_n$,
  (f) substituted phenylS(O)$_n$ in which the substituents are X and Y,
  (g) halogen,
  (h) hydroxy,
  (i) $C_{1-10}$ alkoxy,
  (j) $C_{1-5}$ alkocycarbonyl,
  (k) $C_{1-5}$ acyloxy,
  (l) phenyl, and
  (m) substituted phenyl in which the substituents are X and Y;
(7) phenyl;
(8) substituted phenyl in which the substituents are X and Y;
(9) amino;
(10) $C_{1-5}$ alkylamino;
(11) di($C_{1-5}$ alkyl)amino;
(12) phenylamino;
(13) substituted phenylamino in which the substituents are X and Y;
(14) phenyl $C_{1-10}$ alkylamino;
(15) substituted phenyl$C_{1-10}$alkylamino in which the substituents are X and Y;
(16) a member selected from
  (a) piperidinyl,
  (b) pyrrolidinyl,
  (c) piperazinyl,
  (d) morpholinyl, and
  (e) thiomorpholinyl; and
(17) $R_5S$ in which $R_5$ is selected from
  (a) $C_{1-10}$ alkyl,
  (b) phenyl, and
  (c) substituted phenyl in which the substituents are X and Y;
$R'_4$ is $CH_3$, $CH_2TO$ or H;
X and Y are independently selected from:
  (a) OH,
  (b) halogen,
  (c) trifluoromethyl,
  (d) $C_{1-3}$alkoxy,
  (e) $C_{1-3}$alkylcarbonyloxy,
  (f) phenylcarbonyloxy,
  (g) $C_{1-3}$alkoxycarbonyl,
  (h) phenyloxycarbonyl,
  (i) hydrogen;
  (j) $C_{1-5}$alkyl;
a is a single bond or a double bond provided that when M is C-Z, a is a single bond.
6. A compound according to claim 5 wherein:
M is

Z is Br;
$R_1$ is selected from:
(1) $C_{1-10}$ alkyl;
(2) substituted $C_{1-10}$ alkyl in which one or more substituents(s) is selected from
  (a) halogen,
  (b) hydroxy,
  (c) $C_{1-10}$ alkoxy,
  (d) $C_{1-5}$ alkoxycarbonyl,
  (e) $C_{1-5}$ acyloxy,
  (f) $C_{3-8}$ cycloalkyl,
  (g) phenyl,
  (h) substituted phenyl in which the substituents are X and Y, and
  (i) oxo;
(3) $C_{3-8}$ cycloalkyl;
(4) substituted $C_{3-8}$ cycloalkyl in which one substituent is selected from
  (a) $C_{1-10}$ alkyl,
  (b) substituted $C_{1-10}$ alkyl in which the substituent is selected from
    (i) halogen,
    (ii) hydroxy,
    (iii) $C_{1-10}$ alkoxy
    (iv) $C_{1-5}$ acyloxy,
    (v) $C_{1-5}$ alkoxycarbonyl,
    (vi) phenyl, (vii) substituted phenyl in which the substituents are X and Y, and
(viii) oxo,
(c) halogen,
(d) hydroxy,
(e) $C_{1-10}$ alkoxy,
(f) $C_{1-5}$ alkoxycarbonyl,
(g) $C_{1-5}$ acyloxy,
(h) phenyl,
(i) substituted phenyl in which the substituents are X and Y;
(5) phenylamino;
(6) substituted phenylamino in which the substituents are X and Y;
(7) phenyl$C_{1-10}$alkylamino; and
(8) substituted phenyl $C_{1-10}$ alkylamino in which the substituents are X and Y;
X and Y are independently selected from
(a) OH,
(b) F,
(c) trifluoromethyl,
(d) $C_{1-3}$alkoxy,
(e) hydrogen;
(f) $C_{1-5}$alkyl.

7. A compound according to claim 6 wherein: $R_1$ is $C_{1-10}$alkyl; $R'_4$ is $CH_3$ or $CH_2TO$.

8. A compound according to claim 7 selected from the group wherein;
(a) $R_1$ is 2-methyl-2-butyl, $R'_4$ is $CH_3$, T is tert-butyldimethylsilyl;
(b) $R_1$ is 2-methyl-2-butyl, $R'_4$ is $CH_2TO$, T is tert-butyldimethylsilyl;
(c) $R_1$ is 2-butyl, $R'_4$ is $CH_3$, T is tert-butyldimethylsilyl;
(d) $R_1$ is 2-butyl, $R'_4$ is $CH_2TO$, T is tert-butyldimethylsilyl.

* * * * *